United States Patent [19]

D'Silva

[11] 4,122,204

[45] Oct. 24, 1978

[54] N-(4-TERT-BUTYLPHENYLTHIOSULFENYL)-N-ALKYL ARYL CARBAMATE COMPOUNDS

[75] Inventor: Themistocles D. J. D'Silva, South Charleston, W. Va.

[73] Assignee: Union Carbide Corporation, New York, N.Y.

[21] Appl. No.: 703,822

[22] Filed: Jul. 9, 1976

[51] Int. Cl.$^2$ .................... C07D 307/86; A01N 9/12; C07D 149/43
[52] U.S. Cl. .................................. 424/285; 424/300; 260/346.73; 560/16
[58] Field of Search .................... 260/346.2 R, 479 C; 424/285, 300; 560/16

[56] References Cited

U.S. PATENT DOCUMENTS

| | | | |
|---|---|---|---|
| 3,632,631 | 1/1972 | Wright | 260/479 C |
| 3,663,594 | 5/1972 | Brown et al. | 260/479 C |
| 3,847,951 | 11/1974 | Kohn et al. | 260/346.2 R |
| 3,914,259 | 10/1975 | Brown | 260/346.2 R |
| 3,980,673 | 9/1976 | Siegle et al. | 260/346.2 R |

OTHER PUBLICATIONS

Black et al., J. of Agr. and Food Chem., vol. 21, No. 5, Sep. 1973, pp. 747–751.

*Primary Examiner*—Henry R. Jiles
*Assistant Examiner*—Bernard Dentz
*Attorney, Agent, or Firm*—Richard C. Stewart

[57] ABSTRACT

N-(4-tert-Butylphenylthiosulfenyl)-N-alkyl aryl carbamate compounds exhibit outstanding activity against mites and insects and extremely low levels of mammalian toxicity as compared to closely related prior art compounds.

15 Claims, No Drawings

N-(4-TERT-BUTYLPHENYLTHIOSULFENYL)-N-ALKYL ARYL CARBAMATE COMPOUNDS

This invention relates to N-(4-tert-butylphenylthiosulfenyl)-N-alkyl aryl carbamate compounds and to their preparation. This invention is also directed to insecticidal and miticidal compositions comprising an acceptable carrier and an insecticidally or miticidally effective amount of a carbamate compound of invention as well as to a method of controlling insects and mites by subjecting them to an insecticidally or miticidally effective amount of a carbamate compound of this invention.

More particularly this invention relates to compounds of the formula:

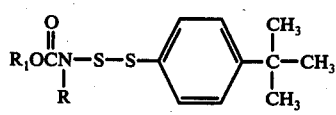

wherein:
R is alkyl;
$R_1$ is naphthyl, 2,3-dihydro-7-benzofuranyl, 2,2-dimethyl-2,3-dihydro-7-benzofuranyl, 2-methyl-2,3-dihydro-7-benzofuranyl or either substituted or unsubstituted phenyl wherein the permissible substituents are one or more fluoro, chloro, bromo, nitro, alkyl, alkoxy, dialkylamino, alkylthio, alkylsulfinyl or alkylsulfonyl substituents.

The compounds of this invention exhibit outstanding miticidal and insecticidal activity. The compounds of this invention are also characterized by unexpectedly reduced mammalian toxicity together with an acceptable level of phytotoxicity in comparison with closely related prior art compounds.

Compounds similar to those described above are known and have been described in the literature. The known compounds differ from the compounds described above primarily in the permissible substituents on the phenylthiosulfenyl moiety. The phenylthiosulfenyl moiety of the prior art compounds may be substituted with up to two fluoro, chloro, bromo or alkyl substituents in any position whereas the phenylthiosulfenyl moiety of the compounds of this invention is substituted with a t-butyl group in the 4-position. The prior art compounds are described in U.S. Pat. No. 3,914,259.

In terms of mammalian toxicity the N-(4-methylphenylthiosulfenyl) derivative, the only N-(4-alkylphenylthiosulfenyl) derivative actually described in the prior art, appears to exhibit a slight numerical advantage in mammalian toxicity in comparison with its parent carbamate compound on a weight basis. This difference in mammalian toxicity is slight and such a difference as does exist appears to be within the limits of experimental accuracy. The mammalian toxicity data for the N-(4-methylphenylthiosulfenyl) derivative and its parent carbamate compound clearly indicate that these compounds as a class have the disadvantage of being extremely toxic to mammals which greatly precludes their use for pest control on important economic food crops. I have found that a very specific class of N-(4-tert-butylphenylthiosulfenyl) carbamate compounds described by the above generic formula are dramatically superior to the N-(alkylphenylthiosulfenyl) carbamate compounds of the prior art and to their parent carbamate compound in terms of dramatically reduced mammalian toxicity. The mammalian toxicity of a representative N-(4-tert-butylphenylthiosulfenyl) compound of the present invention is reduced by a factor of 23 in comparison with the corresponding N-(4-methylphenylthiosulfenyl) derivative and by a factor 38 in comparison with the parent carbamate compound on a weight basis.

In general, R and $R_1$ individually may not include more than eight aliphatic carbon atoms. Preferred because of their higher level of insecticidal and miticidal activity, and extremely low mammalian toxicity are the compounds of this invention wherein R is methyl and $R_1$ is 2,2-dimethyl-2,3-dihydrobenzofuranyl or phenyl substituted with one or more alkoxy substituents.

One preferred compound of this invention is N-methyl-N-(4-tert-butylphenylthiosulfenyl)-2,3-dihydro-2,2-dimethyl-7-benzofuranyl carbamate, due to its extremely low mammalian toxicity, exceptionally high level of insecticidal activity against aphid, south armyworm and bean beetle and its low phytotoxicity against important economic crops. The second preferred compound according to this invention is [N-methyl-N-(4-tert-butylphenylthiosulfenyl)]-2-isopropoxy phenyl carbamate which also exhibits a very low level of mammalian toxicity, extremely low phytotoxicity and outstanding pesticidal activity against mites and insects.

The compounds of this invention can be prepared in accordance with the following general reaction scheme:

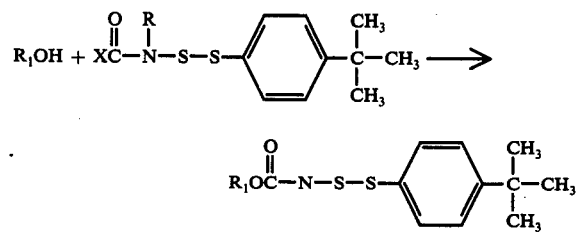

wherein $R_1$ and R are as defined above and X is fluorine or chlorine.

This reaction is usually carried out by bringing together substantially equimolar amounts of the reactants in an inert solvent in the presence of an acid acceptor. Any inert solvent can be employed in the conduct of this reaction. Illustrative of inert solvents which are useful in this reaction are benzene, toluene, xylene, dioxane, tetrahydrofuran, ethyl ether, cyclohexane, methylene chloride or the like.

The acid acceptor employed in the conduct of this reaction is a basic material that can be either an organic or an inorganic base. The molar ratio of the acid acceptor to either reactant is substantially equimolar although a slight excess of acid may be employed if desired. Inorganic bases, such as sodium hydroxide, potassium hydroxide or the like and organic bases such as tertiary amines, alkali metal alkoxides or the like are illustraative of bases which are useful as acid acceptors in this reaction. Preferred acid acceptors are tertiary amines, such as triethylamine, pyridine, 1,4-diazabicyclo[2.2.2] octane or the like.

This reaction can be conducted in either a homogeneous phase system or a heterogeneous phase system. In the latter case, a phase transfer agent, such as a crown ether or a quaternary ammonium halide, can be used to facilitate the transfer of the reactants across the phase interface.

Reaction temperatures are not critical and may be varied over a wide temperature range depending to a large extent on the reactivity and the thermal stability of the reactants. In most cases the reaction goes to completion at room temperature. However, if either reduced or extended reaction times are desired, the reaction can be conducted at a temperature of from about $-50°$ C. to about $100°$ C. The preferred reaction temperature range is from about $0°$ C. to about $40°$ C.

Reaction pressures are not critical. For convenience the reaction is usually conducted at atmospheric or autogeneous pressure.

Naphthol, dihydrobenzofuranol and phenolic reactants are well known compounds that can either be obtained from commerical sources or prepared according to methods known to those skilled in the art.

N-Alkyl-N-(4-tert-butylphenylthiosulfenyl) carbamoyl halide compounds utilized as reactants in the preparation of the compounds of this invention can be prepared by a variety of conventional methods. One preferred method of preparing N-alkyl-N-(4-tert-butyl-phenylthiosulfenyl) carbamoyl fluoride reactants is by reacting hydrogen fluoride with an appropriately substituted isocyanate to form the mono-substituted N-alkylcarbamoyl fluoride compound which is then reacted with 4-tert-butylphenylthiosulfenyl chloride in the presence of an acid acceptor to form the desired carbamoyl fluoride compound. For example, methyl isocyanate can be treated with hydrogen fluoride in toluene to form N-methylcarbamoyl fluoride which, in turn, can be reacted in situ with 4-tert-butylphenylthiosulfenyl chloride in the presence of an equivalent amount of triethylamine as the acid acceptor to form N-methyl-N-(4-tert-butylphenylthiosulfenyl) carbamoyl fluoride. Another preferred method of preparing carbamoyl halide reactants is by reacting the corresponding N-sulfenyl chloride compound with an appropriately substituted mercaptan in the presence of an acid acceptor. The above disclosed reactions together with other reactions which are useful in the preparation of carbamoyl halide reactants are described in more detail in my copending U.S. Pat. application Ser. No. 486,631 entitled CARBAMOYL HALIDE COMPOSITIONS filed July 8, 1974.

The following specific examples are presented to more particularly illustrate the manner in which the compounds of this invention may be prepared.

EXAMPLE I

Preparation of 2,2-Dimethyl-2,3-dihydro-7-[N-methyl-N-(4-tert-butylphenylthiosulfenyl)carbamoyloxy] benzofuran To a solution of 4.0 g (0.024 m) of 2,2-dimethyl-2,3-dihydrobenzofuran-7-ol and 6.56 g (0.024 m) of N-methyl-N-(p-tert-butylphenylthiosulfenyl)carbamoyl fluoride in 25 ml of dioxane was added 2.45 g (0.024 m) of triethylamine. After 24 hours the reaction mixture was diluted with 200 ml of water and the product was extracted in ethylacetate. The organic extract was washed in turn with diluted sodium hydroxide and water, dried over $MgSO_4$ and concentrated under reduced pressure. The product was crystallized from isopropyl ether to yield 4.0 g of a white solid, m.p. $150°-151°$ C.

Anal: Calc'd. for $C_{22}H_{27}NO_3S_2$: C, 63.27; H, 6.52; N, 3.35; Found: C, 63.08; H, 6.31; N, 3.43

EXAMPLE II

Preparation of 2-Isopropoxy-[N-methyl-N-(4-tert-butylphenylthiosulfenyl)carbamoyloxy]benzene To a solution of 4.0 g (0.026 m) of 2-isopropoxyphenol and 7.11 g (0.026 m) of N-methyl-N-(p-tert-butylphenylthiosulfenyl)carbamoyl fluoride in 75 ml of toluene was added 2.63 g (0.026 m) of triethylamine. After stirring for 48 hours the reaction mixture was washed with water and dried over anhydrous $MgSO_4$. The product was purified by dry column chromatography to give 2.5g of a white solid. m.p. $84°-85°$ C.

Anal: Calc'd for $C_{21}H_{27}NO_3S_2$: C, 62.19; H, 6.71; N, 3.45; Found: C, 62.23; H, 6.65; N, 3.57

The following compounds are representative of other compounds that are within the scope of this invention which can be prepared according to this invention by selecting appropriate starting materials for use in the procedures described herein above:

3,5-Dimethyl-4-dimethylamino-[N-Hexyl-N-(4-t-butylphenylthiosulfenyl)carbamoyloxy]benzene.

1-[N-propyl-N-(4-t-butylphenylthiosulfenyl)carbamoyloxy]naphthalene.

3-Butyl-4-ethylthio-[N-methyl-N-(4-t-butylphenylthiosulfenyl)carbamoyloxy]benzene.

2,4-Dimethyl-6-propylsulfenyl-[N-butyl-N-(4-t-butylphenylthiosulfenyl)carbamoyloxy]benzene.

2-Chloro-4-nitro-6-ethylsulfonyl-[N-methyl-N-(4-t-butylphenylthiosulfenyl)carbamoyloxy]benzene.

3,5-Difluoro-4-isopropoxy-[N-pentyl-N-(4-t-butylphenylthiosulfenyl)carbamoyloxy]benzene.

2-t-Butoxy-[N-methyl-N-(4-t-butylphenylthiosulfenyl)carbamoyloxy]benzene.

3-Isopropyl -[N-methyl-N-(4-t-butylphenylthiosulfenyl)carbamoyloxy]benzene.

3,4-Dichloro-6-methyl-[N-methyl-N-(4-t-butylphenylthiosulfenyl)carbamoyloxy]benzene.

3-Bromo-4-ethylhexylamino-[N-t-butyl-N-(4-t-butylphenylthiosulfenyl)carbamoyloxy]benzene.

2-Methyl-2,3-dihydro-7-[N-methyl-N-(4-t-butylphenylthiosulfenyl)carbamoyloxy]benzofuran.

2,3-Dihydro-7-[N-methyl-N-(4-t-butylphenylthiosulfenyl)carbamoyloxy]benzofuran.

Selected species of the new compounds were evaluated in comparison with known similar prior art compounds to determine their pesticidal activity against mites and certain insects, including an aphid, a caterpillar, a beetle and a fly. The new compounds were further evaluated for mammalian toxicity.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentration in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-papercovered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and numphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality countr of motile forms was made. Microscopic examination for motile forms was made on the leaves of the test plants. Any individual which was capable of locomotion upon prodding was considered living.

Mammalian Toxicity

These compounds were also evaluated to determine their peroral toxicity to mammals by conventional methods. The animal selected for this experiment was the rat. The test results obtained are expressed in terms of the number of milligrams of compound per kilogram of weight of the animal required to achieve a mortality rate of 50 percent ($LD_{50}$).

The results of these experiments are summarized and set forth in Table I below.

Compound 1 in Table I is the parent N-methyl carbamate compound of the 2,3-dihydro-7-benzofuranyl carbamate compounds of this invention. Compound 1 is known by the generic name Carbofuran and is a well known widely used commercial pesticide. Compound 2 is the 4-methyl phenylthiosulfenyl derivative of the parent compound which has previously been described in the literature. Compound 3 is the 4-tert-butylphenylthiosulfenyl derivative of this invention. Compounds 3 and 4 are the preferred species according to this invention, due to their overall dramatically superior biological properties. Compound 5 is the parent N-methyl carbamate compound of the alkoxyphenyl carbamate compound of this invention.

In Table I are presented insect and rat toxicity data (bait tests) on a comparative basis of the compounds described above. The toxicity is reported in ppm required for a 50% kill ($LD_{50}$).

than its parent and also that both compounds exhibit unacceptable levels of mammaliam toxicity. This high level of mammalian toxicity virtually precludes their use as pest control agents on economically important food crops. These results are to be contrasted with the mammalian toxicity values exhibited by the novel 4-tert-butylphenylthiosulfenyl derivatives of this invention. Compound 3 had a $LD_{50}$ value of 453.0 as compared to 8-14 for the parent compound (compound 1) and 20 for the known 4-methylphenylthiosulfenyl derivative (compound 2) and as such is at least 38 times less toxic to mammals than its parent compound and at least 23 times less toxic to mammals than the previously known 4-methylphenythiosulfenyl derivative. Compound 4 has a $LD_{50}$ value of greater than 640 whereas compound 5, its parent carbamate compound, had a $LD_{50}$ value of 95-104. At the same time it should be noted that the compounds of this invention exhibit low levels of toxicity against important economic crops. The new compounds of this invention are unique among this entire class of compounds in their dramatically superior biological properties, such as insect toxicity, phytotoxicity and mammalian toxicity, the characteristics which are critically determinitive of the ultimate utility of agricultural pesticides.

It will be understood that the insect species employed in the above tests are merely representative of a wide variety of pests that can be controlled by use of the novel compounds of this invention.

The N-(4-tert-butylphenylthiosulfenyl)carbamate compounds contemplated in this invention may be applied as insecticides and miticides according to methods known to those skilled in the art. Pesticidal compositions containing the compound of this invention as the active toxicant will usually comprise a carrier and/or diluent, either liquid or solid.

Suitable liquid diluents or carriers include water, petroleum distilates, or other liquid carriers with or without surface active agents. Liquid concentrates may be prepared by dissolving one of these compounds with

TABLE I

| | | Biological Data in $Ld_{50}$'s | | | | | |
|---|---|---|---|---|---|---|---|
| No. | Structure | Aphid | Mite | Southern Armyworm | Mexican Bean Beetle | House Fly | Rat $LD_{50}$ mg/kg |
| 1 | 2,2-Dimethyl-2,3-dihydro-7-(N-methylcarbamoyloxy)benzofuran | 2 | 175 | 90 | 12 | 12 | 8-14 |
| 2 | 2,2-Dimethyl-2,3-dihydro-7-[N-methyl-N-(4-methylphenyl-thiosulfenyl)carbamoyloxy]benzofuran | 1.4 | 130 | ~25 | 4 | 21 | 20.0 |
| 3 | 2,2-Dimethyl-2,3-dihydro-7-[N-methyl-N-(4-t-butylphenyl-thiosulfenyl)carbamoyloxy]benzofuran | 3 | >500 | 40 | 5 | <17 | 453.0 |
| 4 | 2-Isopropoxy-[N-methyl-N-(4-t-butylphenylthiosulfenyl)carbamoyloxy]benzene | 22 | >500 | 250 | 11 | 110 | 640 |
| 5 | 2-Isopropoxy-(N-methyl-carbamoyloxy)benzene | 16 | >500 | 500 | 12 | 16 | 95-104 |

Examination of the data presented in Table I confirm the maintenance of insect toxicity of the previously known 4-methylphenylthiosulfenyl derivative at levels generally comparable to those of the parent compounds and even in some cases demonstrating slight improvements. However, the high level of mammalian toxicity of the prior art compounds is not acceptable. Note that the rat $LD_{50}$ (mg/kg) of the parent compound (compound 1) is 8-14 while the rat $LD_{50}$ (mg/kg) of the known N-(4-methylphenythiosulfenyl derivative (compound 2) is 20 indicating that the 4-methylphenylthiosulfenyl derivative is slightly less toxic to mammals a nonphytotoxic solvent such as acetone, xylene or nitrobenzene and dispersing the toxicants in water with the addition of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds or the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants. They may also be used in combination with other pesticidally active compositions.

What is claimed is:

1. A compound of the formula:

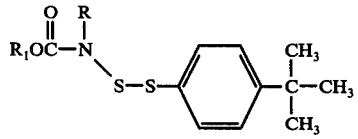

wherein:
R is alkyl of 1-8 carbon atoms;
R₁ is 2,3-dihydro-7-benzofuranyl, 2,2-dimethyl-2, 3-dihydro-7-benzofuranyl, 2-methyl-2,3-dihydro-7-benzofuranyl or phenyl substituted with one or more alkoxy groups of 1-8 carbon atoms.

2. A compound according to claim 1 wherein R is methyl.

3. A compound of the formula:

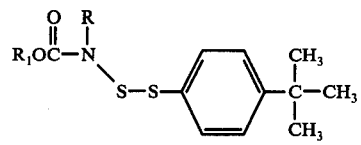

wherein:
R is alkyl of 1-8 carbon atoms;
R₁ is 2,3-dihydro-7-benzofuranyl, 2,2-dimethyl-2,3-dihydro-7-benzofuranyl or 2-methyl-2,3-dihydrobenzofuranyl.

4. N-Methyl-N-(p-tert-butylphenylthiosulfenyl)-2,3-dihydro-2,2-dimethyl-7-benzofuranyl carbamate.

5. [N-Methyl-N-(p-tert-butylphenylthiosulfenyl)]-2-isopropoxy phenyl carbamate.

6. A miticidal and insecticidal composition comprising an acceptable carrier and as the active toxicant an insecticidally or miticidally effective amount of a compound according to claim 1.

7. A composition according to claim 6 wherein R is methyl.

8. A composition according to claim 6 wherein the active toxicant is N-methyl-N-(p-tert-butylphenylthiosulfenyl)-2,3-dihydro-2,2-dimethyl-7-benzofuranyl carbamate.

9. A composition according to claim 6 wherein the active toxicant is [N-methyl-N-(p-tert-butylphenylthiosulfenyl)]-2-isopropoxyphenyl carbamate.

10. A miticidal and insecticidal composition comprising an acceptable carrier and as the active toxicant a miticidally or insecticidally effective amount of a compound according to claim 3.

11. A method of controlling insects and mites which comprises subjecting them to an insecticidally or miticidally effective amount of a compound according to claim 1.

12. A method according to claim 11 wherein R is methyl.

13. A method according to claim 11 wherein the compound is N-methyl-N-(p-tert-butylphenylthiosulfenyl)-2,3-dihydro-2,2-dimethyl-7-benzofuranyl carbamate.

14. A method according to claim 11 wherein the compound is [N-methyl-N-(p-tert-butylphenylthiosulfenyl)]-2-isopropoxyphenyl carbamate.

15. A method of controlling insects and mites which comprises subjecting them to an insecticidally or miticidally effective amount of a compound according to claim 3.

* * * * *

UNITED STATES PATENT OFFICE
CERTIFICATE OF CORRECTION

Patent No. 4,122,204          Dated October 24, 1978

Inventor(s) Themistocles D.J. D'Silva

It is certified that error appears in the above-identified patent and that said Letters Patent are hereby corrected as shown below:

Column 2, line 60, which reads "illustraative" should read -- illustrative --.

Column 7, line 7, which reads "countr" should read -- count --.

Column 7, Table I, line 42, which reads "Biological Data in $Ld_{50}$'s" should read -- Biological Data in $LD_{50}$'s --.

Signed and Sealed this

Sixteenth Day of January 1979

[SEAL]

Attest:

RUTH C. MASON
Attesting Officer

DONALD W. BANNER
Commissioner of Patents and Trademarks